United States Patent [19]

Albright et al.

[11] 4,246,275

[45] Jan. 20, 1981

[54] ANTILIPIDEMIC PARA-[THIENYL AND FURYL (ALKYL OR ALKENYL)AMINO]-BENZOIC ACID DERIVATIVES

[75] Inventors: Jay D. Albright, Nanuet; Thomas G. Miner, Chester; Robert G. Shepherd, South Nyack, all of N.Y.

[73] Assignee: American Cyanamid Company, Stamford, Conn.

[21] Appl. No.: 82,374

[22] Filed: Oct. 5, 1979

Related U.S. Application Data

[63] Continuation-in-part of Ser. No. 557,550, Mar. 12, 1975, Pat. No. 4,185,115.

[51] Int. Cl.³ .................. A61K 31/34; A61K 31/38; C07D 307/54; C07D 333/24
[52] U.S. Cl. .................. 424/275; 260/347.3; 260/347.4; 424/285; 542/423; 549/77
[58] Field of Search ............ 260/347.3, 347.4; 549/77; 424/275, 285; 542/423

[56] References Cited

U.S. PATENT DOCUMENTS 4,192,884   3/1980   Wagner et al. .............. 424/275

OTHER PUBLICATIONS

Fedorov et al., Chem. Abs., vol. 68 (1968) 104869k.
Ferlux, Chemical Abstracts, vol. 78 (1973) 29,493j.
Ferlux, Chemical Abstracts, vol. 81 (1974) 25,703s.
Ferlux, Chemical Abstracts, vol. 83 (1975) 113,925n.

*Primary Examiner*—Richard Raymond
*Attorney, Agent, or Firm*—Jack W. Richards

[57] ABSTRACT

Novel para-[thienyl and furyl(alkyl or alkenyl)amino]-benzoic acids, esters, pharmaceutically acceptable salts and pharmaceutical compositions thereof and a method of lowering serum-lipid levels in mammals therewith.

7 Claims, No Drawings

ANTILIPIDEMIC PARA-[THIENYL AND FURYL (ALKYL OR ALKENYL)AMINO]-BENZOIC ACID DERIVATIVES

CROSS-REFERENCE TO RELATED APPLICATION

This application is a continuation-in-part of our co-pending application Ser. No. 557,550, filed Mar. 12, 1975, now U.S. Pat. No. 4,185,115.

BACKGROUND OF THE INVENTION

Considerable effort has been directed in recent years toward obtaining substances which are useful in the treatment of hyperlipidemia, a condition associated with elevated serum-lipid levels, e.g., elevated cholesterol, phospholipid and/or triglyceride serum levels. This condition is associated with a number of diseases, one of the most serious being atherosclerosis. Medicaments used to lower cholesterol, phospholipid and triglyceride serum levels are termed hypolipidemic or antilipidemic drugs. Presently three major lipid-lowering agents are available: clofibrate, D-thyroxine, and nicotinic acid. [R. I. Levy and D. S. Fredrickson, Postgraduate Medicine, Vol. 47, pps. 130–136 (1970)]. The class of lipid-lowering compounds encompassed by the present invention may be referred to as para-[thienyl and furyl(alkyl or alkenyl)amino]benzoic acid derivatives.

U.S. Pat. No. 3,716,644 discloses and claims a method of lowering serum-lipid levels in mammals by the administration of certain (meta and para alkoxy)benzoic acids, esters, pharmaceutically acceptable salts and pharmaceutical compositions thereof. U.S. Pat. No. 3,868,416 discloses and claims certain 4-(monoalkylamino)benzoic acids, esters, pharmaceutically acceptable salts, pharmaceutical compositions thereof and a method of lowering serum-lipid levels in mammals therewith. German Pat. No. 716,668 discloses the compound p-[(3-phenylpropyl)amino]benzoic acid, however, no utility other than that in a chemical process is given for the compound. The compound p-benzylaminobenzoic acid is disclosed in Chemical Abstracts 42:5033b, 43:1345i, 45:2487e, 48:649b, 48:32846c and 49:10886g; ethyl p-benzylaminobenzoate in Chemical Abstracts 38:P2346[2], 51:8720g and J. Org. Chem. 26:1437 (1961); p-[(p-methoxybenzyl)amino]benzoic acid in J. Chem. Soc. 1088 (1970); ethyl p-($\beta$-phenethylamino)benzoate and p-($\beta$-phenethylamino)benzoic acid in Chemical Abstracts 40:559[3]; and the compound p-[$\beta$-(3,4-dimethoxyphenyl)ethylamino]benzoic acid in Chemical Abstracts 54:13154g. No prior art is known which discloses the para-[thienyl and furyl(alkyl or alkenyl)amino]benzoic acid derivatives of this invention and/or their utility as antilipidemic agents.

SUMMARY OF THE INVENTION

This invention is concerned with and contemplates as novel antilipidemic compounds those compounds which may be referred to as para-[thienyl and furyl(alkyl or alkenyl)amino]benzoic acid derivatives and which may be represented by the formula:

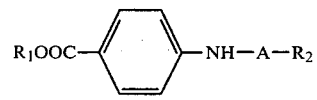

wherein $R_1$ is selected from the group hydrogen, lower alkyl, benzyl, diloweralkylaminoethyl and loweralkoxyethyl; $R_2$ is selected from the group substituted or unsubstituted thienyl and furyl; A is selected from the group $C_nH_{2n}$, wherein $n = 1–16$ and $C_nH_{2n-2}$, wherein $n = 3–16$; the pharmaceutically acceptable acid addition salts thereof; and when $R_1 = H$, the alkali metal or organic basic carboxylic acid salts thereof.

Suitable lower alkyl groups contemplated by this invention are those having 1–6 carbon atoms, as, for example, methyl, ethyl, isopropyl, propyl, tert-amyl and n-hexyl. Suitable lower alkenyl groups contemplated are allyl, 1, 2 or 3-butenyl, and pentenyl. Suitable $C_nH_{2n}$ and $C_nH_{2n-2}$ groups are both branched and straight chain. Suitable substituted thienyl and furyl groups include, for example, halothienyl, dihalothienyl, alkylthienyl, dialkylthienyl, halofuryl, dihalofuryl, alkylfuryl and dialkylfuryl.

As a method of lowering serum-lipid levels in mammals, this invention contemplates and comprises orally administering to said mammals an effective lipid-lowering amount of a para-[thienyl and furyl(alkyl or alkenyl)amino]benzoic acid derivative of the formula:

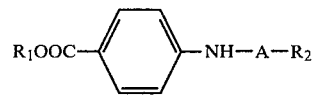

wherein $R_1$ is selected from the group hydrogen, lower alkyl, benzyl, diloweralkylaminoethyl and loweralkoxyethyl; $R_2$ is selected from the group substituted or unsubstituted thienyl and furyl; A is selected from the group $C_nH_{2n}$, wherein $n = 1–16$ and $C_nH_{2n-2}$, wherein $n = 3–16$; the pharmaceutically acceptable salts thereof; and when $R_1 = H$, the alkali metal or organic base carboxylic acid salts thereof.

This invention also contemplates a therapeutic composition in unit-dosage form which is useful to lower serum-lipid levels in mammals comprising a para-[thienyl and furyl-(alkyl or alkenyl) amino]enzoic acid derivative of the formula:

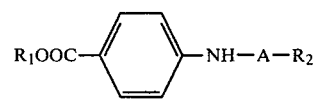

wherein $R_1$ is selected from the group hydrogen, lower alkyl, benzyl, diloweralkylaminoethyl and loweralkoxyethyl; $R_2$ is selected from the group substituted or unsubstituted theinyl and furyl; A is selected from the group $C_nH_{2n}$, wherein $n = 1–16$ and $C_nH_{2n-2}$, wherein $n = 3–16$; the pharmaceutically acceptable salts thereof; and when $R_1 = H$, the alkali metal or organic base carboxylic acid salts thereof, in concentration per dosage unit to provide a daily dosage of from about 35 mg. to about 2.8 g., preferably from about 140 mg. to about 2.0 g.; and a pharmaceutical carrier.

DETAILED DESCRIPTION OF THE INVENTION

The novel para-[thienyl and furyl(alkyl or alkenyl)-amino]benzoic acid derivatives of the present invention are in general colorless or tan crystalline solids with some being colorless or tan oils. The compounds are soluble in organic solvents such as benzene, chloroform, dichloromethane, N,N-diemthylformamide, dimethylsulfoxide and lower alkanols. They are bases and may be converted to their non-toxic addition salts with acids such as sulfuric, hydrochloric, phosphoric, succinic, citric and the like. The compounds wherein $R_1$ is hydrogen may be reacted with alkali bases such as sodium hydroxide and potassium hydroxide or with organic bases such as ammonium hydroxide, pyridine, mono-, di-, or tri-lower alkalamines such as methylamine, diethylamine, trimethylamine, dibutylamine and the like to obtain the corresponding carboxylic acid salts.

The novel para-[thienyl and furyl (alkyl or alkenyl)-amino]benzoic acid derivatives of this invention are prepared by reacting lower alkyl p-aminobenzoates with alkylating agents such as thienyl- or furylalkyl or thienyl- or furylalkenyl halides, thienyl- or furylalkanol or thienyl- or furylalkenol O-sulfates, O-tosylates, O-trifluoromethyl-sulfanoates, O-methanesulfonates with or without solvent at 50° C. to 150° C. Suitable solvents are hexamethylphosphoramide, N,N-dimethylformamide, N,N-dimethylacetamide, lower alkanols, chloroform, dimethylsulfoxide, benzene, xylene, acetonitrile and the like. The reaction may be carried out with an equivalent of base such as an alkali carbonate or bicarbonate.

Alternatively, the thienyl and furyl alkyl or thienyl and furyl alkenyl aminobenzoates may be prepared by reaction of a lower alkyl p-aminobenzoate with a thienyl- or furyl-alkyl or thienyl- or furylalkenyl halide, in the presence of an equivalent of sodium hydride in an inert solvent such as hexamethylphosphoramide, N,N-dimethylformamide, N,N-dimethylacetamide and xylene at 50° C. to 150° C. In the case of the chlorides the alkylation of lower alkyl p-aminobenzoates may be carried out in an inert solvent such as hexamethylphosphoramide, N,N-dimethylformamide and N,N-dimethylacetamide with an equivalent of dry sodium iodide or potassium iodide to promote the reaction.

The p-(thienyl or furyl alkylamino) and p-(thienyl or furyl alkenylamino) benzoic acids are prepared by hydrolysis of the corresponding benzoate esters by reacting with an alkali metal hydroxide such as sodium potassium hydroxide in a lower alkanol, water or an aqueous lower alkanol at 25° C. to 100° C. Alternatively, the acids may be prepared by hydrolysis of the lower alkyl benzoates with mineral acids such as hydrochloric, hydrobromic sulfuric, in water or aqueous lower alkanols.

Esters of p-(thienyl and furyl alkylamino) and p-(thienyl and furyl alkenylamino) benzoic acids may be prepared by conversion of the appropriate acid to an acid chloride with reagents such as thionyl chloride and oxalyl chloride and then reacting the intermediate acid chloride with lower alkanols, dilower alkylaminoethanol, lower alkoxyethanol and the like.

Alternatively, the novel thienyl and furyl alkylaminobenzoates may be prepared by reductive alkylation of a lower alkyl p-aminobenzoate or p-aminobenzoic acid with a suitable thienyl- or furylalkyl-aldehyde or ketone in the presence of noble metals and (or) nickel or cobalt catalysts or a suitable metal hydride. For example, Raney nickel hydrogen and an thienyl- or furylalkylaldehyde may be used to reductively alkylate ethyl p-aminobenzoate. Auxiliary catalysts such as aluminum chloride, piperidine acetate or acids may be used in reductive alkylation. Similarly, thienyl- or furylalkenylaminobenzoates may be prepared by reductive alkylation of a suitable thienyl- or furylalkenylaldehyde or ketone in the presence of noble metals and (or) nickel or cobalt catalyst or a suitable metal hydride.

EXAMPLE 1

Preparation of 4-(2-Thienyl)butanol

To 240 ml. of 1 M borane in tetrahydrofuran chilled in an ice bath, is added dropwise, 20.4 g. of 4-(2-thienyl)-butyric acid in 50 ml. of tetrahydrofuran. After the addition, the mixture is allowed to stand at room temperature for 17 hours and is poured onto ice. After standing, the mixture is extracted with ether, the ether extract washed with water, dried over magnesium sulfate and concentrated in vacuo to give a pale yellow oil.

EXAMPLE 2

Preparation of Ethyl p-[4-(2-Thienyl)butylamino]benzoate

To a solution of 15.6 g. of 4-(2-thienyl)butanol and 20.9 ml. (15.2 g.) of triethylamine in 500 ml. of dichloromethane, cooled to −8° C. is added 8.45 ml. (12.5 g.) of methanesulfonyl chloride dropwise over 10 minutes. The mixture is stirred at −8° C. for 25 minutes, washed with 4000 ml. of ice water, 200 ml. of cold 10% CHI, 200 ml. of cold saturated sodium bicarbonate and 200 ml. of cold saturated sodium chloride solution. The organic layer is dried over magnesium sulfate and concentrated in vacuo to an oil. This oil is combined with 33 g. of ethyl p-aminobenzoate and 80 ml. of hexamethylphosphoramide and the mixture heated in an oil bath at 105°–110° C. for 19 hours. The solution is chilled, diluted with 35 ml. of water, chilled, 20 ml. of ethanol is added and the mixture is filtered. The solid is washed with ethanol-water (1:1) and with water and the damp solid recrystallized from 150 ml. of ethanol to give tan crystals, m.p. 63°–65° C. Recrystallization from ethanol gives tan crystals, m.p. 65°–67° C.

EXAMPLE 3

Preparation of p-[4-(2-Thienyl)butylamino]benzoic Acid

A mixture of 7.5 g. of ethyl p-[4-(2-thienylbutyl)-amino]benzoate (prepared as described in Example 38), 7.5 g. of potassium hydroxide and 150 ml. of ethanol-water (9:1) is refluxed for 4 hours. The mixture is acidified while hot with concentrated hydrochloric acid, diluted with water, cooled and filtered. The solid is washed with water to give tan crystals, m.p. 137°–140° C. Recrystallization from ethanol gives tan crystals, m.p. 139°–141° C.

EXAMPLE 4

Preparation of 2-(2-Thienyl)ethanol O-Methanesulfonate

A mixture of 12.8 g of 2-(2-thienyl)ethanol, 450 ml. of dichloromethane and 20.2 g. of triethylamine is chilled to −10° C. and 12.8 g. of cold methanesulfonyl chloride is added dropwise over 30 minutes. After stirring for 1 hour, the mixture is washed with 300 ml. of cold water, 300 ml. of cold 10% hydrochloric acid, 300 ml. of cold saturated sodium bicarbonate, and 300 ml. of cold saturated sodium chloride solution. The organic layer is dried over magnesium sulfate and concentrated under vacuum to give the product as an oil.

EXAMPLE 5

Preparation of Ethyl 4-[2-(2-thienyl)ethylamino]benzoate

A mixture of 33.0 g. of ethyl p-aminobenzoate, 21.8 g. of 2-(2-thienyl)ethanol O-methanesulfonate (prepared as described in Example 49) and 100 ml. of hexamethylphosphoramide is heated in an oil bath at 125° C. for 16 hours. The mixture is chilled, diluted with 15 ml. of ethanol and 150 ml. of water. The mixture is extracted with ether and the ether extracts washed with water, dried over magnesium sulfate and concentrated in vacuo to give a crude oil. A sample of this oil is chromatographed over silica gel and the fractions containing the product are combined and recrystallized from hexane to give ethyl 4-[2-(2-thienyl)ethylamino]benzoate as yellow-tan crystals, m.p. 93°-95° C.

EXAMPLE 6

Preparation of 4-[2-(2-Thienyl)ethylamino]benzoic Acid

A mixture of 29.7 g. of crude ethyl 4-[2-(2-thienyl)-ethylamino]benzoate, 20 g. of potassium hydroxide and 200 ml. of 95% ethanol is refluxed for 3 hours. The solution is diluted with 100 ml. of water and adjusted to pH 6 with concentrated hydrochloric acid. The mixture is cooled, filtered and the solid washed with ethanol-water (1:1) to give a solid. The solid is heated with 200 ml. of ethanol, filtered and the filtrate concentrated. Purification gives the product, m.p. 163°-165° C.

The compounds of the present invention show hypolipidemic activity in mammals, specifically warm-blooded animals. The mechanism of action of these compounds is not known and the inventors do not wish to be limited to any particular mechanism. However, the compounds of the present invention were shown to possess hypolipidemic activity as determined by animal experiments as follows: The compounds were administered orally admixed with the diet to groups of 4-6 male rats, CFE strain from Carworth Farms. A control group of 6-8 rats was maintained on the diet alone; test groups were maintained on the diet plus the indicated percentage of compound by weight. After 6 days treatment serum sterol concentrations were determined either (1) according to the saponification and extraction method of P. Trinder, Analyst 77, 321 (1952) and the colorimetric determination of Zlatkis, et al., J. Lab. Clin. Med. 44, 486 (1953) or (2) by the extraction method of H. H. Leffler, Amer. J. Clin. Path. 31 310 (1959), the overall method appropriately modified for use with an automatic mechanical analyzer. Serum triglycerides were estimated by the automated procedure of Kessler and Lederer ["Automation in Analytical Chemistry", Skeggs, L. T., (Ed.), Mediad, Inc., New York, 1965 p. 341]. In these tests a compound is considered to have hypolipidemic activity if it depresses the serum sterol level below that of the controls, and/or depresses triglyceride levels below controls. Table I shows representative compounds of the present invention and the degree to which they depress serum sterols and triglyceride levels after a one-week dosing period.

TABLE I

| COMPOUND | % Compound in Diet | Lowering of Serum Sterol | Lowering of Serum Triglyceride |
|---|---|---|---|
| p-[4-(2-thienyl)butylamino]benzoic acid | 0.1 | 23 | 10 |
| Ethyl p-[4-(2-thienyl)butylamino]benzoate | 0.1 | 10 | 0 |
| 4-[2-(2-thienyl)ethylamino]benzoic acid | 0.1 | 18 | 37 |
| Ethyl 4-[2-(2-thienyl)ethylamino]benzoate | 0.1 | 15 | 31 |

The compounds of the present invention are useful as hypolipidemic agents in mammals when administered in amounts ranging from about 0.5 mg. per kg. to about 40 mg. per kg. of body weight per day. A preferred dosage regimen for optimum results would be from about 2 mg. per kg. to about 29 mg. per kg. of body weight per day. Thus the daily dosage employed for a subject of about 70 kg. is about 35 mg. to about 2.8 g. and preferably about 140 mg. to about 2.0 g.

The active compounds of the present invention may be orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafters, chewing gum or the like. Such compositions and preparations should contain at least 0.1% of active compound. The percentage in the compositions and preparations may, of course, be varied and may conveniently be between about 5% and 75% or more or the weight of the unit. The amount of active compound in such therapeutically useful compositions or preparations is such that a suitable dosage will be obtained. Preferred compositions or preparations are prepared so that an oral dosage unit form contains between about 10 mg. and 500 mg. of active compound.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring. When the dosage unit form is a capsule, it may contain in addition to materials of the above type a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Any material used in preparing any dosage-unit form should be pharmaceutically pure and substantially non-toxic in the amounts employed. In addition, the active ingredients may be incorporated into sustained release preparations.

We claim:

1. A para-[thienyl or furyl(alkyl or alkenyl)amino]benzoic acid derivative of the formula:

wherein $R_1$ is selected from the group hydrogen, lower alkyl, benzyl, diloweralkylaminoethyl and loweralkoxyethyl; $R_2$ is selected from the group halofuryl, dihalofuryl, alkylfuryl, dialkylfuryl, thienyl or furyl; A is selected from the group $C_nH_{2n}$, wherein n=1–16, with the provision that when n is 1, $R_2$ is not thienyl $C_nH_{2n-2}$, wherein n=3–16; the pharmaceutically acceptable salts thereof; and when $R_1$ is hydrogen, the alkali metal or organic base carboxylic acid salts thereof.

2. The compound according to claim 1, p-[(4-([2-thienyl]butyl)amino]benzoic acid.

3. The compound according to claim 1, p-[(4-[2-furyl]butyl)amino]benozic acid.

4. The compound according to claim 1, ethyl p-[(4-[2-thienyl]butyl)amino]benzoate.

5. The compound according to claim 1, p-([2-(2-thienyl)ethylamino]benzoic acid.

6. The compound according to claim 1, ethyl p-[2-(2-thienyl)ethylamino]benzoate.

7. A method of lowering serum-lipid levels in mammals which comprises orally administering to said mammals an effective amount of a para-[thienyl and furyl(alkyl or alkenyl)amino]benzoic acid derivative of the formula:

wherein $R_1$ is selected from the group hydrogen, lower alkyl, benzyl, diloweralkylaminoethyl and loweralkoxyethyl; $R_2$ is selected from the group halofuryl, dihalofuryl, alkylfuryl, dialkylfuryl, thienyl or furyl; A is selected from the group $C_nH_{2n}$, wherein n=1–16, with the proviso that when n is 1, $R_2$ is not thienyl and $C_nH_{2n-2}$, wherein n=3–16; the pharmaceutically acceptable salts thereof; and when $R_1$ is hydrogen, the alkali metal or organic base carboxylic acid salts thereof.

* * * * *